United States Patent
Cho et al.

(10) Patent No.: US 11,719,624 B2
(45) Date of Patent: Aug. 8, 2023

(54) LIQUID IMMERSION MICRO-CHANNEL MEASUREMENT DEVICE AND MEASUREMENT METHOD WHICH ARE BASED ON TRAPEZOIDAL INCIDENT STRUCTURE PRISM INCIDENT-TYPE SILICON

(71) Applicant: KOREA RESEARCH INSTITUTE OF STANDARDS AND SCIENCE, Daejeon (KR)

(72) Inventors: Hyun Mo Cho, Daejeon (KR); Yong Jai Cho, Daejeon (KR); Won Chegal, Daejeon (KR)

(73) Assignee: KOREA RESEARCH INSTITUTE OF STANDARDS AND SCIENCE, Daejeon (KR)

( * ) Notice: Subject to any disclaimer, the term of this patent is extended or adjusted under 35 U.S.C. 154(b) by 1105 days.

(21) Appl. No.: 16/464,792

(22) PCT Filed: Dec. 15, 2016

(86) PCT No.: PCT/KR2016/014720
§ 371 (c)(1),
(2) Date: May 29, 2019

(87) PCT Pub. No.: WO2018/101528
PCT Pub. Date: Jun. 7, 2018

(65) Prior Publication Data
US 2019/0346363 A1  Nov. 14, 2019

(30) Foreign Application Priority Data
Nov. 30, 2016 (KR) ........................ 10-2016-0161948

(51) Int. Cl.
*G01N 21/05* (2006.01)
*B01L 3/00* (2006.01)
(Continued)

(52) U.S. Cl.
CPC ........ *G01N 21/05* (2013.01); *B01L 3/502715* (2013.01); *G01N 21/21* (2013.01);
(Continued)

(58) Field of Classification Search
CPC .. G01N 21/05; G01N 21/21; G01N 33/54366; G01N 21/211;
(Continued)

(56) References Cited

U.S. PATENT DOCUMENTS

| 8,940,538 B2* | 1/2015 | Cho ..................... G01N 21/211 436/95 |
| 10,921,241 B2* | 2/2021 | Cho .................. B01L 3/502715 |
| 2015/0253243 A1 | 9/2015 | Cho et al. |

FOREIGN PATENT DOCUMENTS

| JP | 2006058873 | 3/1994 |
| JP | 2009204476 | 9/2009 |

(Continued)

*Primary Examiner* — Christopher L Chin
(74) *Attorney, Agent, or Firm* — Allen, Dyer, Doppelt + Gilchrist, P.A.

(57) ABSTRACT

The present invention relates to a liquid immersion micro-channel measurement device and measurement method which are based on trapezoidal incident structure prism incident-type silicon, and according to one embodiment of the present invention, the liquid immersion micro-channel measurement device based on trapezoidal incident structure prism incident-type silicon comprises: a micro-channel structure including a support and at least one micro-channel, which is formed on the support and has a sample detection layer to which a first bioadhesive material for detecting a first sample is fixed; a quadrangular pyramid-shaped prism formed on the upper part of the micro-channel structure; a sample injection unit for injecting, into the micro-channel, a buffer solution containing the first sample; a polarized light generation unit for emitting incident light polarized through the prism on the micro-channel at an incident angle that (Continued)

satisfies a p-wave non-reflection condition; and a polarized light detection unit for detecting, from the polarized incident light, a polarization change in a first refection light reflected from the sample detection layer, wherein the prism completely reflects, from the polarized incident light incident on the prism, on an upper boundary surface of the prism, second reflection light reflected from a lower boundary surface of the prism and a boundary surface of the buffer solution injected into the micro-channel.

18 Claims, 8 Drawing Sheets

(51) Int. Cl.
  *G01N 21/21* (2006.01)
  *G01N 33/543* (2006.01)
  *G01N 21/03* (2006.01)
(52) U.S. Cl.
  CPC ...... *G01N 33/54366* (2013.01); *B01L 2300/0654* (2013.01); *B01L 2300/0663* (2013.01); *G01N 21/211* (2013.01); *G01N 2021/0378* (2013.01); *G01N 2021/052* (2013.01)

(58) Field of Classification Search
  CPC ..... G01N 2021/0378; G01N 2021/052; G01N 21/55; G01N 2021/213; G01N 33/54373; G01N 35/08; G01N 21/554; G01N 2021/558; B01L 3/502715; B01L 2300/0654; B01L 2300/0663; B01L 2300/163; B01L 2300/168; B01L 2300/0809; B01L 2300/0861
  USPC ................ 356/246, 937; 385/130, 131, 132; 422/82.05, 82.11, 502; 435/288.7, 808, 435/973; 436/524, 805, 164
  See application file for complete search history.

(56) References Cited

FOREIGN PATENT DOCUMENTS

| JP | 2011209097 | 10/2011 | |
| KR | 101383652 | 4/2014 | |
| KR | 101383652 B1 * | 4/2014 | ............ G01N 21/05 |

* cited by examiner

[FIG. 1]
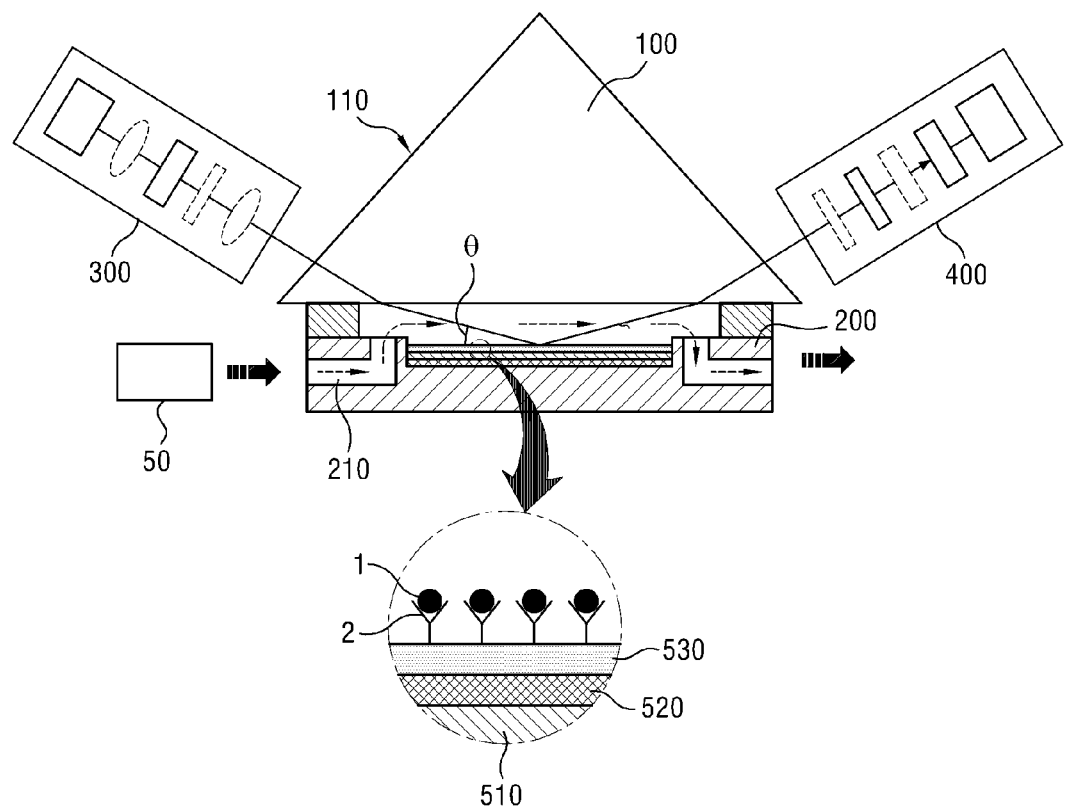

【FIG. 2】
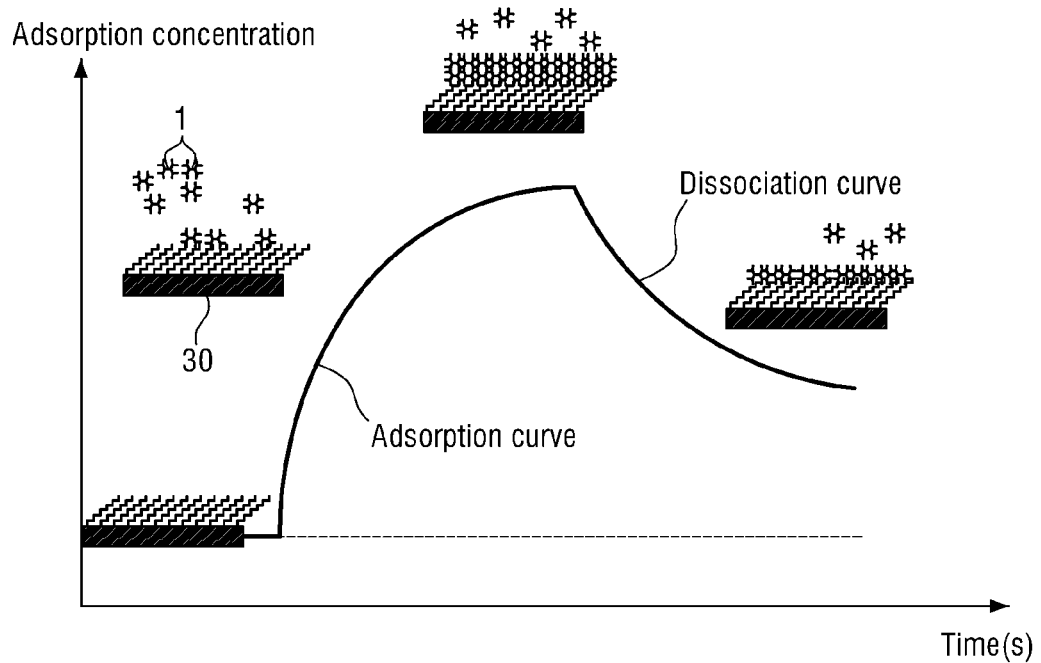
【FIG. 3】
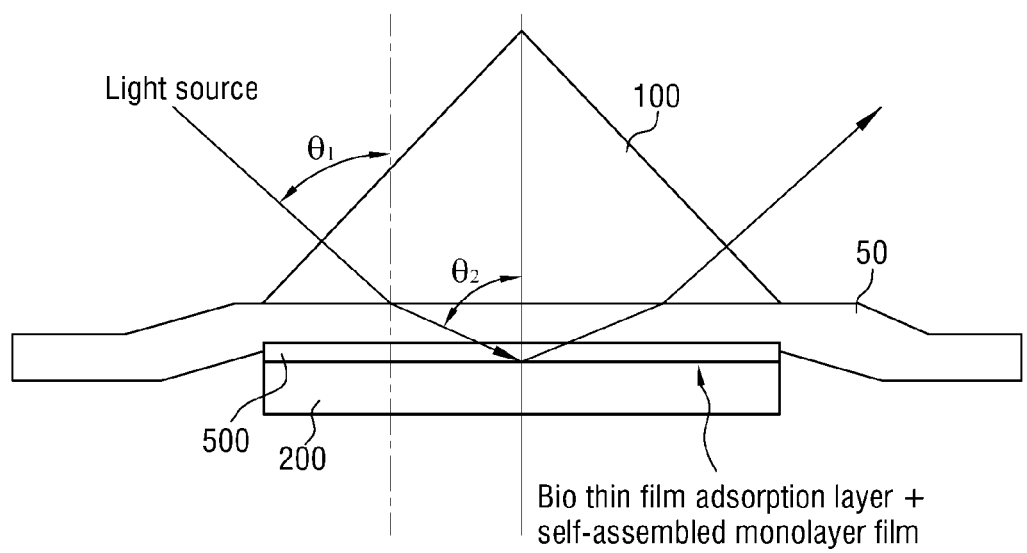

[FIG. 4]
Wavelength of light source:655nm
Refractive index of buffer solution medium:n=1.333,n=1.3332
Bio thin film adsorption layer + self-assembled monolayer film:4nm,n=1.45
Refractive index of substrate material:n=3.8391,k=0.018186
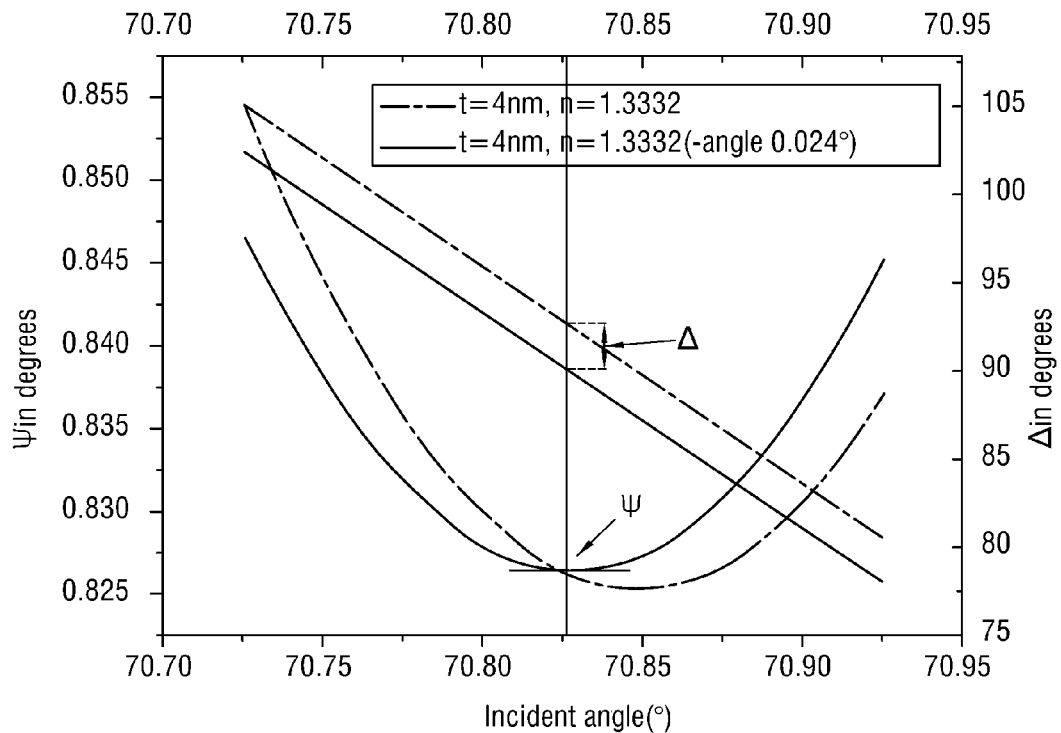

[FIG. 5]
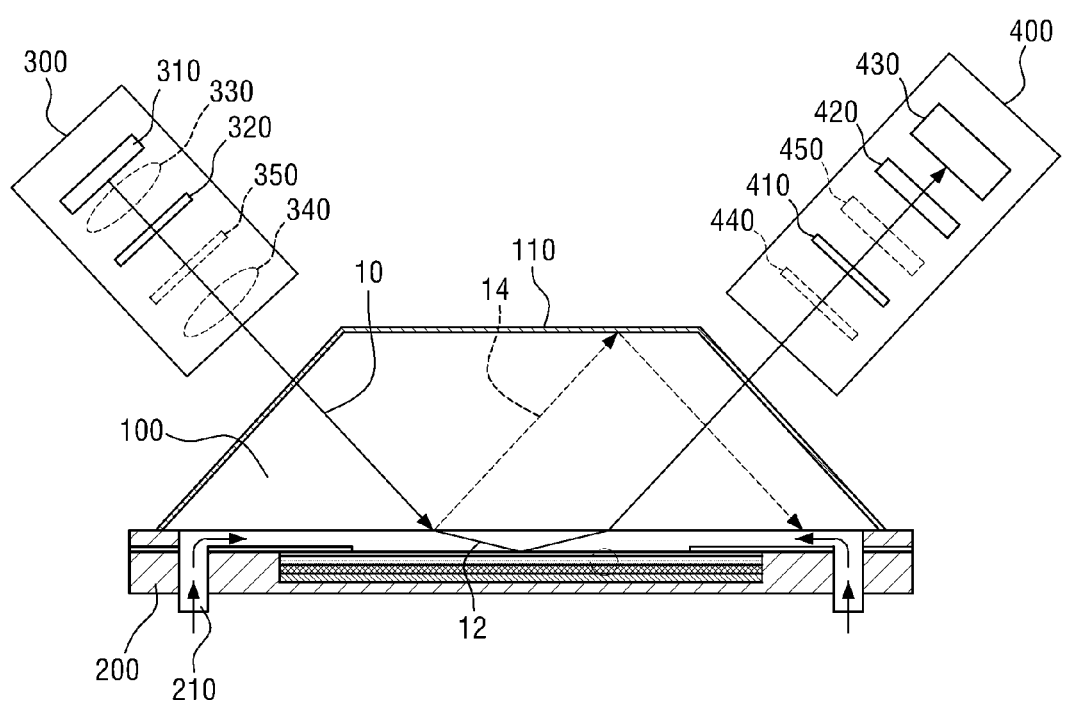
[FIG. 6A]
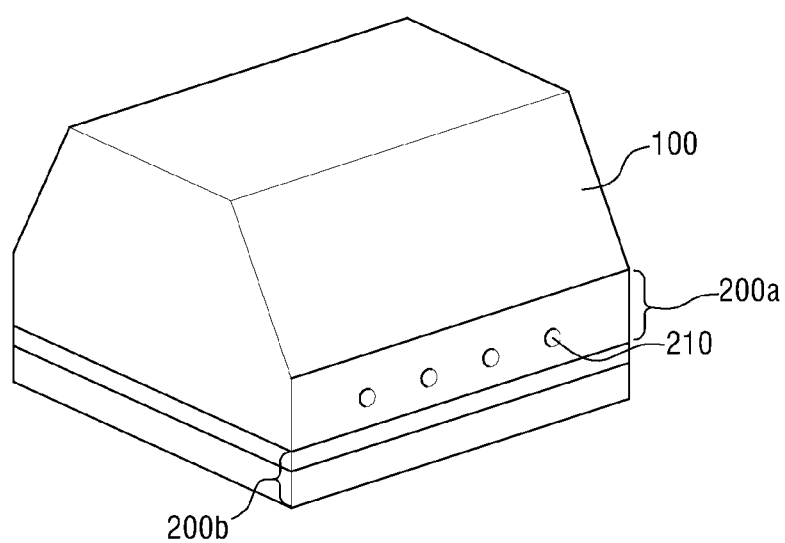

[FIG. 6B]
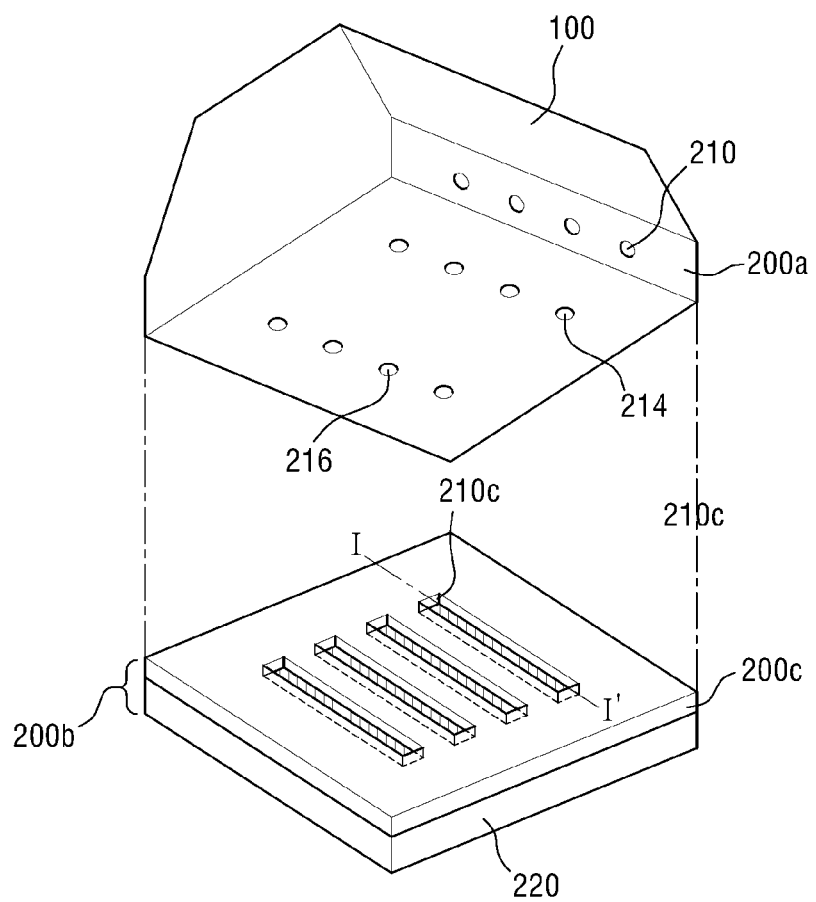

【FIG. 7】
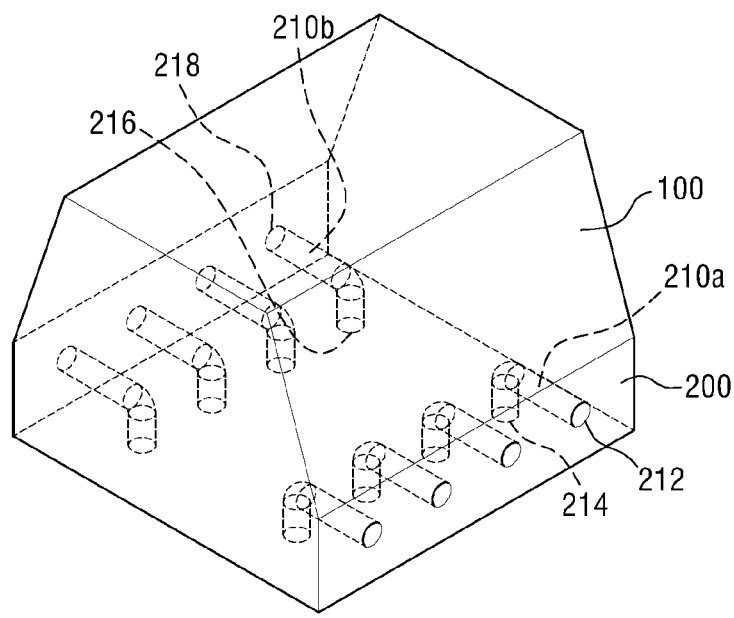
【FIG. 8】
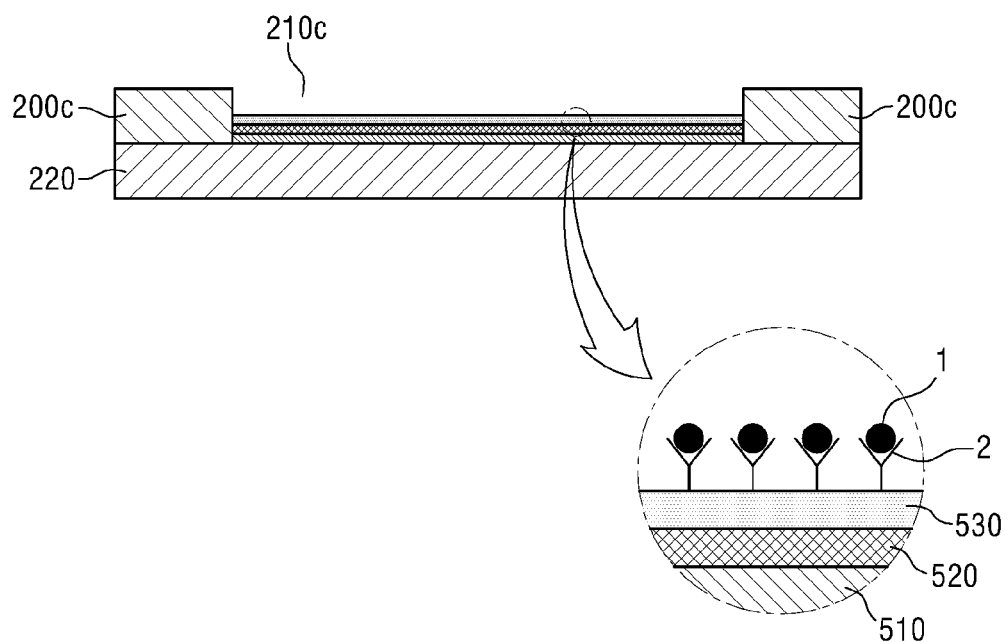

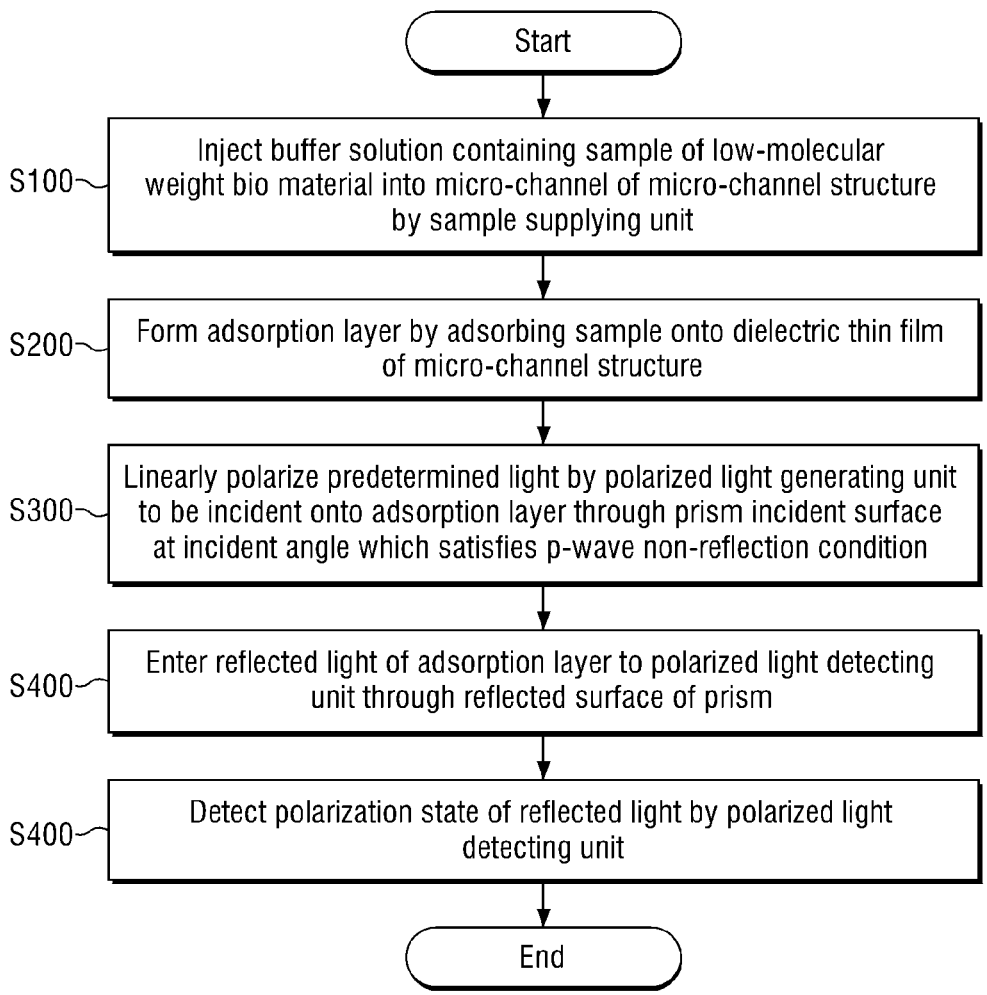
[FIG. 9]

[FIG. 10A]
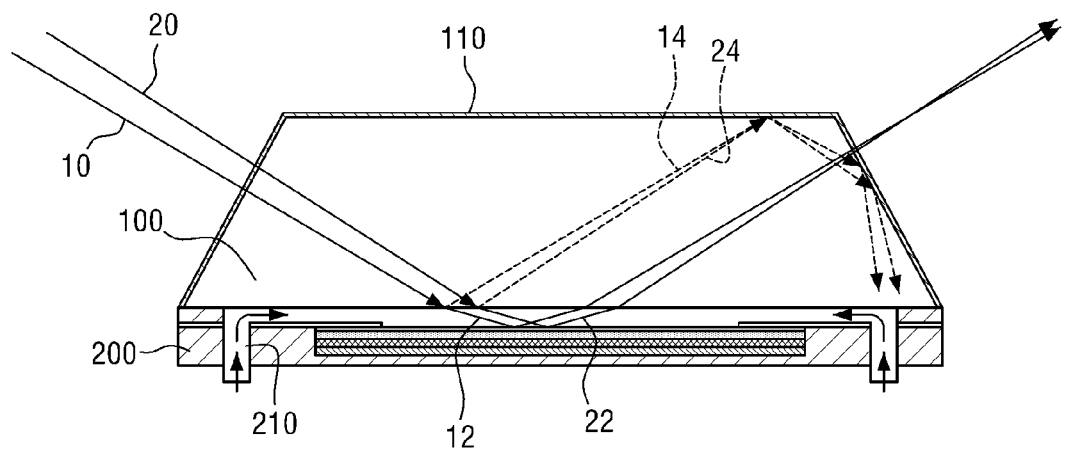
[FIG. 10B]
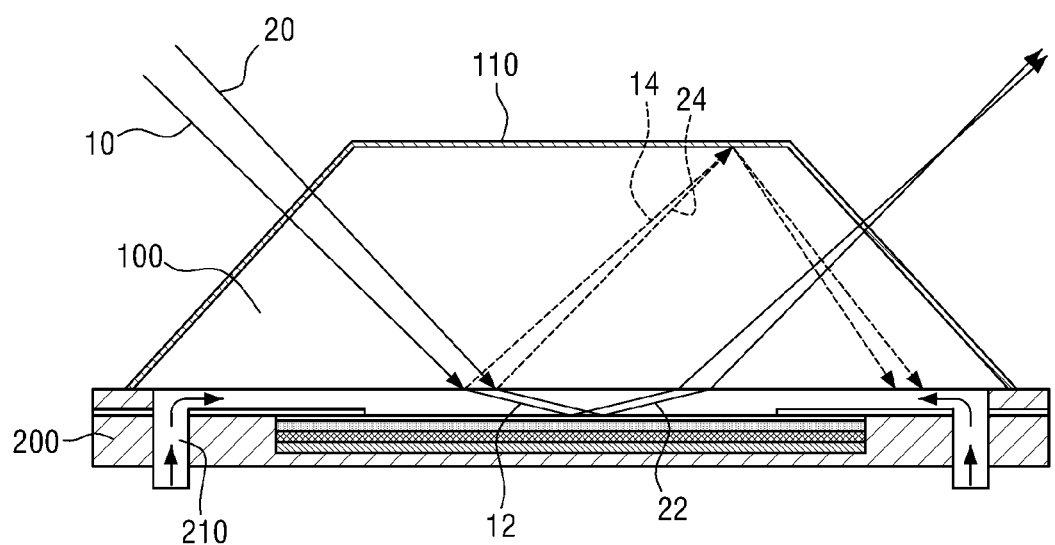

LIQUID IMMERSION MICRO-CHANNEL MEASUREMENT DEVICE AND MEASUREMENT METHOD WHICH ARE BASED ON TRAPEZOIDAL INCIDENT STRUCTURE PRISM INCIDENT-TYPE SILICON

TECHNICAL FIELD

The present invention relates to a liquid immersion micro-channel measurement device and a measurement method which are based on a trapezoidal incident structure prism incident-type silicon.

BACKGROUND ART

Reflectometry and ellipsometry are optical analysis techniques which measure a change of the reflectance or a polarization state of reflected light reflected from a surface of a sample and analyze the measured value to find a thickness and optical properties of the sample.

Measurement equipment using the same includes a reflectometer and an ellipsometer. The measurement equipment is utilized to evaluate thicknesses and physical properties of various nano-level thin films during a process of manufacturing a nano-thin film of a semiconductor industry. Further, efforts are continuing to expand an application range to a bio industry to apply them to interface analysis of biomaterials such as proteins, DNA, viruses, and new drug materials.

The reflectometer of the related art is sufficient to evaluate a thickness and a physical property of a nano thin film having a size of several nanometers (nm) or larger. However, there is a problem in that measurement sensitivity for analyzing a low molecular weight bio material requiring sensitivity in the range of approximately 1 to 0.001 nanometer is low so that the reliability is degraded. As compared with the reflectometer, the ellipsometer has measurement sensitivity of 0.01 nm or lower. Especially, the measurement sensitivity is high in the condition that the refractive index is comparatively large as in the case of measuring the thickness of the oxide film having a relatively small refractive index as compared with the semiconductor on the high refractive index semiconductor substrate.

However, in order to analyze the low molecular biomaterial using the ellipsometer, a measurement method with improved sensitivity is required.

As a technique of the related art for improvement of the measurement sensitivity at the time of analyzing the biomaterial, a surface plasmon resonance sensor (hereinafter, referred to as an "SPR" sensor) in which a reflectometry and a surface plasmon resonance technique are combined is known.

The surface plasmon resonance (SPR) phenomenon is known as a phenomenon that when electrons on a metal surface are excited by light waves to be collectively vibrated in a normal direction of the surface, light energy is absorbed at this time. It is known that the SPR sensor can not only measure the thickness and the refractive index change of the nano-thin film which is in contact with the metal surface using the surface plasmon resonance phenomenon sensitive to a polarization characteristic of the light, but also measure the change of an adsorption concentration of a bio material in a real time in a non-labeling manner which does not use a fluorescent material.

The SPR sensor is manufactured to have a structure in which a metal thin film of several tens of nanometers is coated on a material such as glass and a biomaterial can be bonded thereto and uses a principle that when a sample dissolved in a buffer solution is bonded to the sensor, a resonance angle is changed. The resonance angle is obtained by measuring the reflectance. When light is incident onto the SPR sensor, the glass material serves as an incident medium and the light passes through a thin film layer to which the biomaterial is bonded so that the buffer solution finally serves as a substrate.

With this structure, a refractive index of the buffer solution corresponding to the substrate material directly affects the shift of the resonance angle as well as the change of the biological thin film layer by the adhesion of the sample to be measured. Therefore, in order to measure only pure binding kinetics, the refractive index of the buffer solution needs to be independently measured and corrected.

In order to correct the change of the refractive index of the buffer solution and prevent the error due to the diffusion between the sample and the buffer solution, a method of correcting the error using a delicate valve device, an air injecting device, and two or more channels in which one is used as a reference channel has been used. However, it is difficult to distinguish the SPR angle change due to the change of the refractive index of the buffer solution from an SPR angle change due to the pure adsorption and dissociation characteristic and it may always act as a factor causing a measurement error. Consequently, due to the limitation of the measurement method as described above, the SPR sensor of the related art has a fundamental difficulty in measuring the adsorption and dissociation characteristic of a material having a small molecular weight such as a small molecule.

Further, the SPR sensor of the related art uses a metal thin film of precious metal such as gold (Au) and silver (Ag) for surface plasmon resonance so that the manufacturing cost of the sensor is expensive. Further, the metal thin film has problems in that the surface roughness is uneven in accordance with the manufacturing process so that the variation of the refractive index is severe, it is difficult to quantitatively measure the biomaterial due to the unstable optical property, and errors caused by different sensitivity characteristics of different positions are included as relatively compared with the reference channel.

In order to improve the disadvantages of the SPR sensor, when a biomaterial adhesive sensor layer is formed on a substrate material such as silicon and an amplitude and a phase of light which passes through a buffer solution under a liquid immersion micro-channel environment to be reflected onto the substrate material are measured by the ellipsometry under a p-wave non-reflection condition, a signal that the measured amplitude is insensitive to the change of the refractive index of the buffer solution but is sensitive to the binding kinetics of the bio material may be obtained. When the junction characteristic of the bio material adsorbed onto the substrate material under the liquid immersion micro-channel environment is measured, contrary to the SPR measurement, the buffer solution serves as an incident medium and light which passes through the bio material adsorption layer is reflected from the substrate material.

Under this measurement condition, a measured ellipsometric angle is insensitive to the change of the refractive index of the incident medium which is a buffer solution, but is sensitive only to the change of the bio thin film and the substrate material. In this case of a substrate having a stable refractive index, such as silicon, the measured ellipsometric angle $\Psi$ obtains a signal which is sensitive only to the change of the bio thin film and an ellipsometric angle $\Delta$ represents a signal which is sensitive only to the refractive index of the buffer solution so that the thickness of the bio thin film and the refractive index of the buffer solution may be simultaneously measured. However, when using a substrate parallel to a planar incidence structure such as a prism, the light reflected from the interface between the prism and the buffer solution needs to be removed and only the light reflected from the substrate needs to be used. In order to minimize a usage amount of the sample, the interval between a prism surface and the substrate material needs to be reduced. In this case, two reflected light are located to be very close, so that it is difficult to separate the light and the light serves as a measurement error. Therefore, a measurement method with a new structure for distinguishing light reflected from the interface between the prism and the buffer solution in a planar incident structure such as a prism from light reflected from the substrate material including a sensor is required.

FIG. 1 is a diagram of a prior patent which manufactures a sensor layer on a substrate material such as silicon and uses ellipsometry under the liquid immersion micro-channel environment in order to improve the problem of the SPR sensor. As illustrated in FIG. 1, a bio material junction characteristic sensor according to the prior patent is approximately configured by a prism 100, a micro-channel structure 200, a polarized light generating unit 300, and a polarized light detecting unit 400. In this case, the micro-channel structure 200 of the biomaterial junction characteristic sensor according to the prior patent disposes an adsorption layer 530 on a substrate 510 or a dielectric thin film 520 to form a liquid immersion micro-channel 210 environment. In this case, when the buffer solution 50 in which a sample 1 of the bio material is dissolved is injected into the micro-channel 210, the biomaterial is adsorbed onto a ligand 2 material formed on a surface of the adsorption layer 530 to form an adsorption layer having a predetermined thickness.

The polarized incident light generated from the polarized light generating unit 300 is incident onto the interface of the buffer solution 50 and the substrate 510 via an incident surface 110 of the prism at an angle which causes the p-wave non-reflection condition. In this case, the reflected light reflected from the substrate 510 includes optical data on the refractive index of the adsorption layer of the sample 1 and the buffer solution. That is, when the sample 1 is adsorbed onto or dissociated from the ligand 2, a molecular binding and dissociation kinetics such as an adsorption concentration, a thickness or a refractive index of the adsorption layer, or a refractive index of the buffer solution is changed and thus the measured ellipsometric angles vary. Further, the reflected light including the optical data is detected by the polarized light detecting unit 400. In this case, the polarized light detecting unit 400 measures the change in accordance with a polarized component of the reflected light, that is, the ellipsometric angles, to figure out the molecular binding and dissociation kinetics of the sample 1 and the refractive index of the buffer solution.

FIG. 2 illustrates an adsorption curve indicating a process of adsorbing the sample 1 onto the metal thin film 30 and a dissociation curve indicating a dissociating process. The larger the association rate constant ka, the faster the absorption of the biomaterial and the smaller the dissociation rate constant kd, the slower the dissociation.

That is, the association rate constant and the dissociation rate constant are measured to calculate a dissociation constant (KD=kd/ka) in an equilibrium state. For example, it is possible to determine whether a new drug candidate material having a low molecular weight which may be used as a carcinogenesis inhibitor can be used as a new drug by measuring a characteristic of the new drug candidate material which is associated onto or dissociated from a protein including a carcinogen-inducing factor.

Hereinafter, the characteristic and the limitation of the biomaterial analysis sensor according to the prior art will be described with reference to FIGS. 3 and 4. When the light is incident using a prism incident structure as illustrated in FIG. 3, the light is incident onto the interface at an inclined angle of approximately 70.85° (=θ2) and when the light is incident from the prison onto the buffer solution by the refractive index change (0.0002) of the buffer solution, the angle change may be approximately −0.024°. The p-wave non-reflection condition is approximately θ2=70.85°. However, the current angle due to the change of the refractive index of the buffer solution is changed to 70.826° which is 0.024° smaller. Therefore, as illustrated in FIG. 4, a graph of Ψ and Δ is represented and the p-wave non-reflection angle is hardly changed in accordance with the change of the refractive index so that values of Ψ and Δ may be measured at 70.826° which is 0.24° smaller.

In FIG. 4, in a solid line graph when the buffer solution 50 has different refractive indexes, the refractive index of the buffer solution 50 is 1.3330 and the dotted line graph corresponds to the refractive index 1.3332 of the buffer solution 50. As the measurement result by the change of the incident angle when the prism structure is used, as illustrated in FIG. 4, the change of the Ψ value acts to cancel the small change in the vertical incident structure so that the change is hardly represented. However, Δ exhibits a large change. The ellipsometric constant Δ for a phase difference is sensitively changed only by the change of the refractive index of the buffer solution but is hardly affected by the junction characteristic, so that only the change of the refractive index of the buffer solution may be measured with high sensitivity. The smaller the thickness of the thin film material, the larger the change of the ellipsometric constant Δ. When the change of the refractive index is measured to be applied for an application study to analyze the change of the physical property or the junction characteristic of the material, it is possible to measure the refractive index with ultra-high sensitivity as compared with the SPR measurement method of the related art.

When a buffer solution which is continuously supplied and a buffer solution in which a refractive index is changed due to the solvent used for the sample are supplied to the sensor through a micro-channel, the pure binding kinetics and the change of the refractive index of the buffer solution may be simultaneously measured.

However, as illustrated in FIG. 3, when the interval between a bottom surface of the prism and the substrate material is small, it is difficult to separate light reflected from the interface of the prism and the buffer solution from light reflected from the substrate material. Since, it is measured under the p-wave non-reflection condition, there may be a problem in that a measurement error is caused due to intensity of the light reflected from the substrate material weaker than that of the light reflected from the interface of the prism and the buffer solution.

DETAILED DESCRIPTION OF THE INVENTION

Technical Problem

The present invention has been made to solve the problem of the related art and an object of the present invention is to provide a liquid immersion micro-channel measurement device and a measurement method with high sensitivity which are based on a trapezoidal incident structure prism incident-type silicon.

Specifically, an object of the present invention is to provide a liquid immersion micro-channel measurement device and a measurement method with high sensitivity based on a trapezoidal incident structure prism incident-type silicon which completely separate light reflected from an interface of a prism and a measurement medium from light reflected from a substrate material using a trapezoidal incident structure prism.

Further, an object of the present invention is to solve the problems of the measurement method of the related art in that light reflected from the interface of the prism and the measurement medium has a higher energy than that of light reflected from the substrate material and is hardly separated therefrom, which may cause the measurement error and when a diaphragm is used to separate light, a measurement range which measures at a different angle which varies depending on the change of the refractive index is limited.

Specifically, in order to minimize the consumption of the sample, another object of the present invention is to provide a liquid immersion micro-channel measurement device and a measurement method based on a trapezoidal incident structure prism incident-type silicon which minimize a height of the channel and provide a micro-channel having a multi-channel so that various experiment conditions which change the concentration of sample or varies an adhesive degree of self-assembled monolayer film can be provided.

Furthermore, an object of the present invention is to provide a liquid immersion micro-channel measurement device and a measurement method based on a trapezoidal incident structure prism incident-type silicon which may measure a bioadhesive material in a non-labeled manner at high sensitivity to be widely utilized in various industries such as bio, medical, food, and environment.

In the meantime, a technical object to be achieved in the present invention is not limited to the aforementioned technical objects, and another not-mentioned technical object will be obviously understood by those skilled in the art from the description below.

Technical Solution

As a technical solution to achieve the above-described technical object, according to a first exemplary embodiment of the present invention, a liquid immersion micro-channel measurement device based on a trapezoidal incident structure prism incident-type silicon includes: a micro-channel structure including a support and at least one micro-channel which is formed on the support and has a sample detecting layer to which a first bioadhesive material is fixed to detect a first sample; a truncated pyramid-shaped prism formed on an upper portion of the micro-channel structure; a sample injecting unit which injects a buffer solution including the first sample into the micro-channel; a polarized light generating unit which irradiates incident light polarized through the prism onto the micro-channel at an incident angle which satisfies a p-wave non-reflection condition; and a polarized light detecting unit which detects a polarization change of first reflected light reflected from the sample detecting layer, among the polarized incident light.

In this case, the prism totally reflects, from the upper interface of the prism, second reflected light which is reflected from an interface of a lower interface of the prism and a buffer solution injected into the micro-channel, among the polarized incident light which is incident onto the prism.

Further, according to a first exemplary embodiment of the present invention, a liquid immersion micro-channel measurement device based on a trapezoidal incident structure prism incident-type silicon includes: a micro-channel structure including a support, a first micro-channel which is formed on the support and has a first sample detecting layer to which a first bioadhesive material is fixed to detect a first sample, and a second micro-channel which has a second sample detecting layer to which a second bioadhesive material is fixed to detect a second sample; a truncated pyramid-shaped prism formed on an upper portion of the micro-channel structure; a sample injecting unit which injects a buffer solution including the first sample or the second sample into the first micro-channel and the second micro-channel; a polarized light generating unit which irradiates incident light polarized through the prism onto the first micro-channel and the second micro-channel at an incident angle which satisfies a p-wave non-reflection condition; and a polarized light detecting unit which detects a polarization change of first reflected light reflected from the first sample detecting layer or the second sample detecting layer, among the polarized incident light.

In this case, the polarized light generating unit includes a beam splitter which divides the incident light into first incident light which is incident onto the first sample detecting layer and second incident light which is incident onto the second sample detecting layer.

Further, the first incident light and the second incident light are refracted to the first micro-channel and the second micro-channel from a lower interface of the prism and then divided into first reflected light reflected from the first sample detecting layer or the second sample detecting layer and second reflected light reflected by the lower interface of the prism and a buffer solution injected into the micro-channel. In this case, the prism totally reflects the second reflected light from the upper interface of the prism.

Further, according to a third exemplary embodiment of the present invention, a liquid immersion micro-channel measurement method based on a trapezoidal incident structure prism incident-type silicon includes: a first step of injecting a buffer solution into a micro-channel structure including at least one micro-channel having a sample detecting layer to which a first bioadhesive material is fixed to detect a first sample by a sample injecting unit; a second step of adsorbing the first sample included in the buffer solution onto a first antibody of the sample detecting layer; a third step of allowing a polarized light generating unit to polarize light to be incident onto the micro-channel at an incident angle which satisfies a p-wave non-reflection condition, through an incident surface of a truncated pyramid-shaped prism formed above the micro-channel structure; a fourth step of allowing the polarized light detecting unit to detect a polarization change of first reflected light reflected from the sample detecting layer, among the polarized incident light; and a fifth step of detecting a concentration of the first sample adsorbed onto the sample detecting layer, based on the polarization change of the first reflected light.

In this case, the prism totally reflects, from the upper interface of the prism, second reflected light which is reflected from an interface of a lower interface of the prism and a buffer solution injected into the micro-channel, among incident light which is incident onto the prism.

Advantageous Effects

As described above, the liquid immersion micro-channel measurement device and the measurement method based on a trapezoidal incident structure prism incident-type silicon according to the present invention may provide a liquid immersion micro-channel measurement device and a measurement method based on a trapezoidal incident structure prism incident-type silicon with high sensitivity.

Specifically, the trapezoidal incident structure prism is used to completely separate light reflected from an interface of the prism and the measurement medium and light reflected from the substrate material to allow high sensitivity measurement.

Further, it is possible to solve the problems of the measurement method of the related art in that light reflected from the interface of the prism and the measurement medium has a higher energy than that of light reflected from the substrate material and is hardly separated therefrom, which may cause the measurement error and when a diaphragm is used to separate light, a measurement range which measures at a different angle which varies depending on the change of the refractive index is limited.

Specifically, it is possible to minimize the consumption of the sample by minimizing the height of the channel.

Furthermore, the micro-channel having a multi-channel is provided so that various experimental conditions may be provided by changing a concentration of the sample to be injected into the multi-channel micro-channel or varying an adsorption degree of the self-assembled monolayer film.

Moreover, the present invention may measure the bioadhesive material in a non-leveling manner under the liquid immersion micro-channel environment at high sensitivity to be widely utilized in various industries such as bio, medical, food, and environment.

Although the present invention has been described in connection with the above-described exemplary embodiments, it will be appreciated by those skilled in the art that various modifications or variations can be made without departing from the gist and the scope of the present invention and it is obvious that the modifications and variations fall within the scope of the appended claims.

In the meantime, a technical object to be achieved in the present disclosure is not limited to the aforementioned effects, and other not-mentioned effects will be obviously understood by those skilled in the art from the description below.

BRIEF DESCRIPTION OF DRAWINGS

FIG. 1 is a cross-sectional view illustrating a sensor for measuring a junction characteristic of a biomaterial known in the prior patent.

FIG. 2 is a schematic diagram illustrating a change in an adsorption concentration during a process of adsorbing and dissociating a sample onto a metal thin film.

FIG. 3 is a schematic diagram of a liquid immersion micro-channel measurement sensor based on a prism incident-type silicon for explaining the problem of the related art.

FIG. 4 is a graph obtained by measuring ellipsometric constants $\Psi$ and $\Delta$ according to adsorption of a biomaterial and the refractive index change of the buffer solution using a sensor for measuring the junction characteristic of a biomaterial known in the prior patent.

FIG. 5 is a schematic view illustrating a configuration of a liquid immersion micro-channel measurement device based on a trapezoidal incident structure prism incident-type silicon according to an exemplary embodiment of the present invention.

FIG. 6 is a view illustrating a trapezoidal incident structure prism and a micro-channel structure according to an exemplary embodiment of the present invention.

FIG. 7 is a perspective view for explaining a trapezoidal incident structure prism and a first structure according to an exemplary embodiment of the present invention in more detail.

FIG. 8 is a cross-sectional view for explaining a second structure according to an exemplary embodiment of the present invention in more detail.

FIG. 9 is a flowchart illustrating a method for simultaneously measuring a molecular junction characteristic and a refractive index of a buffer solution according to the present invention.

FIG. 10 is a view illustrating a path of incident light polarized in a liquid immersion micro-channel measurement device based on a trapezoidal incident structure prism incident-type silicon according to an exemplary embodiment of the present invention.

BEST MODE

Hereinafter, exemplary embodiments of the present invention will be described more fully hereinafter with reference to the accompanying drawings, so as to be easily carried out by those skilled in the art. However, the present invention can be realized in various different forms and is not limited to the exemplary embodiments described herein. Accordingly, in order to apparently describe the present invention, a portion that does not relate to the description is omitted. Like reference numerals designate like elements throughout the specification.

Throughout this specification and the claims that follow, when it is described that an element is "coupled" to another element, the element may be "directly coupled" to the other element or "electrically coupled" to the other element through a third element. In addition, unless explicitly described to the contrary, when a part includes an arbitrary element, it will be understood to imply the inclusion of stated elements but not the exclusion of any other elements. Further, it may be also understood that the presence or addition of one or more other features, numbers, steps, operations, elements, parts, or combinations thereof are not precluded in advance.

Further, in the specification, "unit" includes a unit implemented by hardware, a unit implemented by software, and a unit implemented by both the hardware and the software. Further, one unit may be implemented using two or more hardwares or two or more units may be implemented by one hardware.

In the present specification, some of operations or functions which are described as being performed by a terminal or a device may also be performed by a server connected to the corresponding terminal or device instead. Likewise, some of the operations or functions described as being performed by the server may also be performed on a terminal or device connected to the server.

Configuration of Liquid Immersion Micro-Channel Measurement Device Based on Trapezoidal Incident Structure Prism Incident-Type Silicon Hereinafter, a configuration of a liquid immersion micro-channel measurement device based on a trapezoidal incident structure prism incident-type silicon according to an exemplary embodiment of the present invention will be described in detail with reference to the accompanying drawings.

FIG. 5 is a schematic view illustrating a configuration of a liquid immersion micro-channel measurement device based on a trapezoidal incident structure prism incident-type silicon according to an exemplary embodiment of the present invention.

Referring to FIG. 5, a liquid immersion micro-channel measurement device based on a trapezoidal incident structure prism incident-type silicon according to an exemplary embodiment of the present invention includes a trapezoidal incident structure prism 100, a micro-channel structure 200, a polarized light generating unit 300, and a polarized light detecting unit 400.

The exemplary embodiment of the present invention measures the binding and dissociation kinetics of a bioadhesive material including a low molecular weight material using ellipsometry and has a structure in which a buffer solution (buffer) 50 including a sample (not illustrated) of a bioadhesive material is injected into a micro-channel structure 200. In this case, in the micro-channel structure 200, a micro-channel 210 may be configured by a multi-channel.

First, a trapezoidal incident structure prism 100 refracts light which is incident onto the prism 100. In this case, the sides of the trapezoidal incident structure prism 100 have a trapezoidal shape and form two or more optical planes. Specifically, in the exemplary embodiment of the present invention, the prism 100 may have a truncated pyramid shape.

Therefore, as illustrated in FIG. 5, the liquid immersion micro-channel measurement device based on a trapezoidal incident structure prism incident-type silicon according to the exemplary embodiment of the present invention separately separates light 14 reflected from the interface of the prism 100 and a measurement medium from light 12 reflected from a substrate material to allow high sensitive measurement.

More specifically, the polarized incident light 10 incident from the polarized light generating unit 300 passes through an interface 110 of the trapezoidal incident structure prism 100 and then is divided into light 12 which is refracted at a predetermined angle by a refractive index of a buffer solution 50 flowing through the micro-channel 210 to be incident onto an adsorption layer 530 at a lower interface of the prism 100 and light 14 which is reflected by the lower interface of the prism 100.

In the related art, there is a problem in that it is difficult to separate the light 14 reflected at the interface of the prism 100 and the medium from light 12 which is refracted to be incident onto the adsorption layer 530, and accordingly, the light 14 reflected at the interface between the prism 100 and the medium is refracted and is detected by the polarized light detecting unit 400 together with the light 12 incident on the adsorption layer 530. Therefore, a measurement error is caused by the light 14 having a relatively high energy which is reflected from the interface of the prism 100 and the medium and measurement sensitivity is lowered.

In contrast, according to the exemplary embodiment of the present invention, the prism 100 has a truncated pyramid shape. Therefore, among polarized incident light 10 which is incident by the polarized light generating unit 300, light 14 reflected from the interface of the prism 100 and the medium is totally reflected from the upper interface 110 of the trapezoidal incident structure prism 100 and is not detected by the polarized light detecting unit 400. That is, the polarized light detecting unit 400 detects only the light 12 which is refracted to be incident onto the adsorption layer 530 to be reflected so that it is possible to measure a concentration of a sample which is adsorbed onto or dissembled from the adsorption layer 530 at high sensitivity.

In the meantime, in the exemplary embodiment of the present invention, as a prism, an optical glass may be mainly used, and for example, the prism may be BK7 or SF10, but is not limited thereto.

The micro-channel structure 200 is formed below the trapezoidal incident structure prism 100. Specifically, in the exemplary embodiment of the present invention, the micro-channel structure 200 includes a plurality of micro-channels 210 through which a buffer solution including a sample flows or is discharged. In this case, a width of the micro-channel 210 may be in the range of approximately several micrometers or a micro level which is 1 mm or less. Further, each of the plurality of micro-channels 210 includes an inflow passage 210a, a micro-channel 210c, and an outflow passage 210b. That is, a first micro-channel 210 is formed by connecting the first inflow passage 210a, a first micro-channel 210c, and a first outflow passage 210b.

Hereinafter, the micro-channel structure 200 according to the exemplary embodiment of the present invention will be described in more detail with reference to FIGS. 6 to 8.

FIG. 6A is a view illustrating a trapezoidal incident structure prism and a micro-channel structure according to an exemplary embodiment of the present invention and FIG. 6B is an exploded perspective view illustrating a trapezoidal incident structure prism and a micro-channel structure according to an exemplary embodiment of the present invention.

Further, FIG. 7 is a perspective view for explaining a trapezoidal incident structure prism and a first structure according to an exemplary embodiment of the present invention in more detail. FIG. 8 is a cross-sectional view for explaining a second structure according to an exemplary embodiment of the present invention in more detail.

Referring to FIGS. 6A and 6B, a micro-channel structure according to the exemplary embodiment of the present invention is configured by a first structure 200a and a second structure 200b.

In this case, the first structure 200a is formed below the trapezoidal incident structure prism 100. Specifically, in the exemplary embodiment of the present invention, the above-described trapezoidal incident structure prism 100a and the first structure 200a may be integrally manufactured, but the present invention is not limited thereto. Further, the first structure 200a and the second structure 200b may be separated from each other and the second structure 200b includes a micro-channel layer 200c.

In the meantime, the first structure 200 may be formed of a permeable material such as glass or a transparent synthetic resin material. In this case, an example of a synthetic resin material includes an acrylic resin such as polymethyl methacrylate (PMMA). Further, a silicon-based material such as polydimethylsiloxane (PDMS) may also be used.

More specifically, as illustrated in FIG. 7, the first structure 200a includes a plurality of inflow passages 210a formed on one side of the first structure 200a and a plurality of outflow passages 210b formed on the other side of the first structure. Further, the inflow passage 210a is connected from a first inlet port 212 formed on one side of the first structure to a second inlet port 214 formed in a lower portion of the first structure and the outflow passage 210b is connected from a first outlet port 216 formed in the lower portion of the first structure to a second outlet port 218 formed on the other side of the first structure.

In the meantime, the plurality of inflow passages 210a and the plurality of outflow passages 210b are formed to be connected to the plurality of micro-channels 210c of the micro-channel layer 200c formed in the second structure 200b. Specifically, the second inlet port 214 is formed to be abut against the one side of the micro-channel 210c to connect the first inflow passage 210a to the micro-channel 210c.

Further, the first outlet port 216 is formed to be abut against the other side of the micro-channel 210c to connect the outflow passage 210b to the micro-channel 210c.

That is, the first inflow passage 210a, the first micro-channel 210c, and the first outflow passage 210b are formed to be connected to each other. Therefore, the buffer solution 50 containing the sample injected through the first inflow passage 210a passes through the first micro-channel 210c to be discharged to the first outflow passage 200b.

In other words, the second structure 200b according to the exemplary embodiment of the present invention includes the micro-channel layer 200c and the micro-channel layer 200c includes a plurality of micro-channels 210c. In the meantime, the micro-channel layer 210c may be formed of an acrylic resin such as polymethyl methacrylate (PMMA), but is not limited thereto.

Further, the second structure 200b according to the exemplary embodiment of the present invention includes a sample detecting layer 500 on a bottom surface of a groove formed by the plurality of micro-channels 210c. In this case, the sample detecting layer 500 specifically includes a substrate 510, a dielectric thin film 520 formed on the substrate, and an adsorption layer 530.

The substrate 510 may use silicon Si which has a complex refractive index of approximately 3.8391+i0.018186 at 655 nm and provides constant and stable physical properties with low costs. However, the material of the substrate 510 is not limited thereto and may use a semiconductor or a dielectric material other than silicon.

The dielectric thin film 520 is formed above the substrate. The dielectric thin film 520 uses a transparent thin film material including a semiconductor oxide film or a glass film. In this case, the thickness of the dielectric film is desirably 0 to 1000 nm.

An example of the most common dielectric thin film 520 is a silicon oxide film SiO2 which is obtained by naturally oxidizing silicon to be grown to a thickness of several nanometers. The refractive index of the silicon oxide film is approximately 1.456 at 655 nm which is significantly different from the refractive index of the substrate 510 formed of silicon and helps to increase the measurement sensitivity of the present invention.

Further, the dielectric thin film 520 may use a glass film formed of optical glass. The dielectric thin film 520 which is formed of silicon, the silicon oxide film or the glass film may be manufactured to have a constant refractive index as compared with a metal thin film such as gold and silver, thereby providing a stable optical property and lowering the production cost.

The adsorption layer 530 according to the exemplary embodiment of the present invention may be configured by at least one of a self-assembled thin film and a bio thin film. Further, a bioadhesive material which may detect a specific sample may be fixed to the adsorption layer 530.

In this case, the adsorption layer 530 serves to adsorb or dissociate a sample (not illustrated) of a low-molecular weight bioadhesive material and reflect the incident light.

In other words, the sample included in the buffer solution which flows through the inflow passage 210a may be adsorbed onto the adsorption layer 530 or dissociated from the adsorption layer 530.

Referring to FIG. 5 again, the polarized light generating unit 300 according to the exemplary embodiment of the present invention serves to irradiate the polarized incident light 10 onto the adsorption layer 530 in the micro-channel 210c through the trapezoidal incident structure prism 100 as illustrated in FIG. 5.

The polarized light generating unit 300 includes a light source 310 and a polarizer 320 as essential components and also includes a collimating lens 330, a focusing lens 340 or a first compensator 350.

In this case, the polarizer 320 and the first compensator 350 may be rotatably configured or another polarized light modulating unit may be further included. In the meantime, the polarized incident light has p-wave and s-wave polarized components and light close to a p-wave may be received to increase a signal to noise ratio. In this case, in the present invention, the incident light needs to be irradiated at an incident angle θ which satisfies the p-wave non-reflection condition. A complex reflection coefficient ratio (ρ) in the ellipsometric equation is represented by a ratio of a p-wave reflection coefficient ratio (Rp) to a s-wave reflection coefficient ratio (Rs), that is, ρ=Rp/Rs. The p-wave non-reflection condition means a condition that the p-wave reflection coefficient ratio (Rp) has a value close to 0. The p-wave non-reflection condition is similar to the surface plasmon resonance condition of the SPR sensor of the related art and is a condition that the measurement sensitivity of the present invention is maximized.

The light source 310 irradiates monochromatic light in a wavelength range of infrared, visible or ultraviolet rays or irradiates white light. The light source 310 uses various ramps, light emitting diodes (LED), lasers, laser diodes (LD), and the like. In this case, the light source 310 may include a structure which varies a wavelength depending on a structure of an optical system. In the meantime, an optical signal of reflected light may have relatively smaller intensity in the vicinity of the above-described p-wave non-reflection condition. In this case, the high sensitivity measurement may be allowed by irradiating light at a high quantity using a laser or a laser diode (LD) to increase a signal to noise ratio.

The polarizer 320 has a polarizing plate to polarize light irradiated from the light source 310. In this case, polarized components are a p-wave parallel to an incident surface and an s-wave perpendicular to the incident surface.

The collimating lens 330 receives light from the light source 310 to provide parallel light to the polarizer 320. Further, the parallel light which passes through the polarizer 320 is converged by the focusing lens 340 to increase a quantity of the incident light. Further, the first compensator 350 serves to cause phase lag in the polarized component of the incident light.

As illustrated in FIG. 5, the polarized light detecting unit 400 receives the reflected light 12 reflected from the adsorption layer 530 and detects the change of the polarized state. The polarized light detecting unit 400 includes an analyzer 410, a photo detector 420, and a processor 430 as essential components and optionally includes a second compensator 440 and a spectrometer 450. The analyzer 410, which is a counterpart of the polarizer 320, has a polarizing plate to polarize again the reflected light, thereby controlling a polarization degree of the reflected light or an orientation of a polarizing surface. Further, the analyzer 410 may be rotatably configured depending on the structure of the optical system or may be further provided with a polarization modulating unit which may perform phase change or elimination of polarized components.

The photo detector 420 detects the polarized reflected light to obtain optical data and converts the optical data into an electrical signal. In this case, the optical data includes information on the change of the polarized state of the reflected light. The photo detector 420 may be a CCD-type solid state imaging element, a photomultiplier tube (PMT), or a silicon photodiode.

The processor 430 receives the electrical signal from the photo detector 420 to deduct a measurement value. The processor 430 includes a predetermined interpretation program using reflectometry and ellipsometry so that the processor 430 extracts and interprets the optical data converted to the electrical signal to deduct measurement values such as an adsorption concentration of the sample, a thickness of the adsorption layer 160, an adsorption constant, a dissociation constant, and a refractive index. In order to improve the measurement sensitivity, the processor 430 may desirably deduct the measurement value by calculating the ellipsometric constants $\Psi$ and $\Delta$ for the phase difference of the ellipsometry.

The second compensator 440 delays the phase of the polarized component of the reflected light to control the polarized component. The second compensator 440 may be rotatably configured or optionally include another polarization modulating unit.

When the light source 310 is white light, the spectrometer 450 is used. The spectrometer is used to resolve the reflected light and separate reflected light having a wavelength in a narrow band to send the separated reflected light to the photo detector 420. In this case, the photo detector 420 is a two-dimensional image sensor such as a CCD-type solid state imaging element and obtains optical data on distribution of the reflected light.

Even though not illustrated in the drawing, the exemplary embodiment of the present invention may further include a sample injecting unit. In this case, the sample injecting unit (not illustrated) injects or discharges a buffer solution including a sample or a buffer solution into or from the micro-channel 210.

Measurement Method of Liquid Immersion
Micro-Channel Measurement Device Based on
Trapezoidal Incident Structure Prism Incident-Type
Silicon Hereinafter, a simultaneous measurement method of a molecular junction characteristic and a refractive index of a buffer solution refractive index and a principle thereof will be described with reference to the accompanying drawings.

FIG. 9 is a flowchart illustrating a method for simultaneously measuring a molecular junction characteristic and a refractive index of a buffer solution according to the present invention. As illustrated in FIG. 9, the measurement method of the present invention includes a first step S100 to a fifth step S500.

As illustrated in FIG. 5, in a first step S100, a sample injecting unit dissolves a sample (not illustrated) of a bioadhesive material including a low molecular weight material into a buffer solution 50 and injects the sample in the micro-channel 210 of the micro-channel structure 100. In this case, the sample injecting unit may inject the buffer solution 50 containing samples having different concentrations into the respective multi-channel micro-channels 210.

Further, the sample injecting unit may inject the buffer solution 50 into each of the micro-channels 210 with a time interval. Further, the buffer solution 50 may be injected only into some of the micro-channels 210 and the other micro-channels 210 may not be used.

In a second step S200, a sample (not illustrated) of a bioadhesive material is adsorbed onto a substrate 510 or a dielectric thin film 520 to form an adsorption layer 530.

Differently from this, the sample may be adsorbed on a plurality of adsorption layers on a plurality of different self-assembled monolayer films or identical self-assembled monolayer films formed on the single micro-channel 210c of FIG. 8 to form adsorption layers having different junction characteristics.

In a third step S300, predetermined light irradiated from a light source 310 is polarized by a polarizer 310 and is incident onto the adsorption layer 530 through a trapezoidal incident structure prism 100. In this case, the polarized incident light 10 passes through the trapezoidal incident structure prism 100 and is refracted at a predetermined angle by a refractive index of the buffer solution 50 in the micro-channel 210c located at a lower edge of the prism 100 and then is incident onto the adsorption layer 530. In this case, the polarized incident light has p-wave and s-wave polarized components. In the meantime, the incident light needs to have an incident angle θ which satisfies the p-wave non-reflection condition.

In a fourth step S400, the reflected light reflected from the adsorption layer 530 is incident into the polarized light detecting unit 400 through the prism 100. In this case, the reflected light is an elliptically polarized state. In the meantime, among the polarized incident light 10, the light 14 reflected from the lower interface of the prism is totally reflected from the upper interface of the trapezoidal incident structure prism 100 so that the path of the light 14 is not directed to the polarized light detecting unit 400.

In a fifth step S500, the polarized light detecting unit 400 detects a polarized state of the reflected right. To be more specific, first, the analyzer 410 receives the reflected light which is elliptically polarized on the adsorption layer 530 to pass only light according to the polarization characteristic.

Next, the photo detector 420 detects the change of the polarized component of the reflected light to obtain predetermined optical data, converts the optical data into an electrical signal, and transmits the electrical signal to a processor 430.

Next, the processor 430 including a program using reflectometry or ellipsometry extracts and interprets the optical data converted to the electrical signal to deduct values such as an adsorption concentration of the sample, an adsorption and dissociation constant, a refractive index of the sample, and a refractive index of the buffer solution.

In this case, in the present invention, the processor 430 calculates an ellipsometric constant $\Delta$ on a phase difference of the ellipsometry to measure a measurement value of a refractive index of the buffer solution and measures an ellipsometric constant $\Psi$ on an amplitude ratio to calculate the binding kinetics. This is because the ellipsometric constant $\Delta$ on a phase difference is only sensitive to the refractive index change of the buffer solution and is little affected by the junction characteristics in the p-wave non-reflection condition, so that the refractive index change of the buffer solution may be only measured. Further, the ellipsometric constant $\Psi$ on an amplitude ratio is highly sensitive to the junction characteristics of the material.

Accordingly, the junction characteristics of the sample contained in the buffer solution to flow is measured as $\Psi$ and simultaneously the refractive index change of the buffer solution with the sample dissolved therein or the refractive index change of the buffer solution containing a solvent such as DMSO added for dissolving the sample is determined as Δ, thereby determining only pure junction characteristics.

Experimental Example

FIG. 10 is a view illustrating a path of incident light 10 polarized in a liquid immersion micro-channel measurement device based on a trapezoidal incident structure prism incident-type silicon according to an exemplary embodiment of the present invention.

Specifically, FIG. 10A illustrates an example of a silicon-based liquid immersion micro-channel measurement device including a trapezoidal incident structure prism formed by BK7 and FIG. 10B illustrates an example of a silicon-based liquid immersion micro-channel measurement device including a trapezoidal incident structure prism formed by SF10.

In the related art, there is a problem in that the measurement range at different angles which vary in accordance with the change of the refractive index is limited.

However, as illustrated in FIG. 10, the silicon-based liquid immersion micro-channel measurement device including a trapezoidal incident structure prism according to the exemplary embodiment of the present invention may detect both first incident light 10 and second incident light 20 having different incident angles using a polarized light detecting unit 400. That is, a broader range of incident angle is allowed as compared with the related art and a measurable range for different angles which vary depending on the change of the refractive index is also broadened.

As described above, the liquid immersion micro-channel measurement device based on a trapezoidal incident structure prism incident-type silicon according to the exemplary embodiment of the present invention uses a trapezoidal incident structure to separate and detect only light reflected from the substrate material by totally reflecting light reflected from the interface of the prism and the medium from an upper surface of the trapezoidal prism as a progress direction of the light to achieve high sensitive measurement.

In the measurement method of the related art, the light reflected from the interface of the prism and the measurement medium has a higher energy than the light reflected from the substrate material and is hardly separated to cause a measurement error. Further, when a diaphragm is used to separate the light, there is a problem. However, it is possible to separately separate the light reflected from the interface of the prism and the measurement medium from the light reflected from the substrate material, using the trapezoidal incident structure prism.

In an experiment for a search of a new drug candidate material which needs to minimize the consumption of the sample, a height of a channel needs to be minimized. Further, in the case of the trapezoidal incident structure, the height of the channel may be lowered more than that of the inclined incident structure (a minimum height for an inclined structure is necessary in a structure using an inclination of the interface of the prism and the micro-channel and the silicon surface).

Further, the micro-channel structure of the present invention includes a micro-channel which is combined with a trapezoidal prism structure optimized for analyze of a bioadhesive material and is configured by a single channel in which multi-channel or a plurality of self-assembled monolayer films is formed. Accordingly, various experimental conditions are provided by changing a concentration of the sample to be injected into the multi-channel micro-channel or varying an adsorption degree of the self-assembled monolayer film so that the efficiency of the analysis experiment of the bioadhesive material may be increased.

Further, the present invention may measure the bioadhesive material in a non-leveling manner under the liquid immersion micro-channel environment at high sensitivity to be widely utilized in various industries such as bio, medical, food, and environment. In the meantime, the liquid immersion micro-channel measurement method based on the trapezoidal incident structure prism incident-type silicon according to the exemplary embodiment of the present invention may be implemented in the form of a recording medium including a command which may be executed by a computer such as a program module to be automated. The computer readable medium may be an arbitrary available medium which is accessible by a computer and includes all of volatile and non-volatile media, and removable and non-removable media. Further, the computer readable medium may include all of a computer storage medium and a communication medium. The computer storage medium includes all of volatile and non-volatile media, and removable and non-removable media which are implemented by an arbitrary method or technique for storing information such as a computer readable command, a data structure, a program module, and other data.

For example, the recording medium may include a read-only memory (ROM), a random access memory (RAM), a magnetic tape, a magnetic disk, a flash memory, and an optical data storage device. Further, the computer readable recording medium is distributed in computer systems connected through a computer communication network and a computer readable code is stored therein and executed in a distributed manner.

A communication medium typically includes a computer readable command, a data structure, a program module, or other data of a modified data signal such as a carrier wave or other transmitting mechanism and also includes an arbitrary information transfer medium.

The above-description of the present invention is illustrative only and it is understood by those skilled in the art that the present invention may be easily modified to another specific type without changing the technical spirit of an essential feature of the present invention. Thus, it is to be appreciated that the embodiments described above are intended to be illustrative in every sense, and not restrictive. For example, a component which is described as a singular form may be embodied to be dispersed or components which are dispersed may be embodied to be a combined form.

The scope of the present invention is represented by the claims to be described below rather than the detailed description, and it is to be interpreted that the meaning and scope of the claims and all the changes or modified forms derived from the equivalents thereof come within the scope of the present invention.

That which is claimed is:

1. A liquid immersion micro-channel measurement device based on trapezoidal incident structure prism incident-type silicon, the liquid immersion micro-channel measurement device comprising:
   a micro-channel structure including a support and at least one micro-channel which is formed on the support and has a sample detecting layer to which a first bioadhesive material is fixed to detect a first sample;
   a trapezoidal incident structure prism on an upper portion of the micro-channel structure;
   a sample injecting unit which injects a buffer solution including a first sample into the at least one micro-channel;

a polarized light generating unit which irradiates incident light polarized through the trapezoidal incident structure prism onto the at least one micro-channel at an incident angle which satisfies a p-wave non-reflection condition; and a polarized light detecting unit which detects a polarization change of first reflected light reflected from the sample detecting layer, among polarized incident light;

wherein the trapezoidal incident structure prism totally reflects, from a planarized upper interface of the trapezoidal incident structure prism, second reflected light which is reflected from an interface of a lower interface of the trapezoidal incident structure prism and a buffer solution injected into the at least one micro-channel, among polarized incident light which is incident onto the trapezoidal incident structure prism.

2. The liquid immersion micro-channel measurement device of claim 1, wherein the first reflected light passes in a different direction from second reflected light which passes through an inclined surface of the trapezoidal incident structure prism to be reflected from a bottom of the trapezoidal incident structure prism with respect to an upper edge of the trapezoidal incident structure prism.

3. The liquid immersion micro-channel measurement device of claim 2, wherein the polarized light detecting unit separates the first reflected light from the second reflected light.

4. The liquid immersion micro-channel measurement device of claim 1, further comprising:
an optical device which adjusts a magnitude of the incident light which is incident through the trapezoidal incident structure prism.

5. The liquid immersion micro-channel measurement device of claim 4, wherein the optical device further includes an image forming device for forming a focal point of the incident light on an upper surface of the trapezoidal incident structure prism.

6. The liquid immersion micro-channel measurement device of claim 5, wherein the image forming device comprises one of a lens, a lens system, and a reflector.

7. The liquid immersion micro-channel measurement device of claim 1, wherein the sample detecting layer includes:
a substrate;
a dielectric thin film formed above the substrate; and
an adsorption layer formed above the dielectric thin film;
wherein a first bioadhesive material for detecting the first sample is fixed to the adsorption layer.

8. The liquid immersion micro-channel measurement device of claim 7, wherein the first reflected light further includes light reflected from the dielectric thin film.

9. The liquid immersion micro-channel measurement device of claim 7, wherein the dielectric thin film comprises one of a transparent semiconductor oxide film and a glass film, and a thickness of the dielectric thin film is 0 to 1000 nm.

10. The liquid immersion micro-channel measurement device of claim 7, further comprising:
a concentration calculating unit which calculates a thickness or a concentration of the first sample which is adsorbed onto the adsorption layer based on a polarization change of the first reflected light.

11. The liquid immersion micro-channel measurement device of claim 1, wherein the micro-channel structure further includes a second micro-channel in which a second sample detecting layer to which a second bioadhesive material is fixed to detect a second sample.

12. A liquid immersion micro-channel measurement device based on trapezoidal incident structure prism incident-type silicon, the liquid immersion micro-channel measurement device comprising:
a micro-channel structure including a support, a first micro-channel which is formed on the support and has a first sample detecting layer to which a first bioadhesive material is fixed to detect a first sample, and a second micro-channel which has a second sample detecting layer to which a second bioadhesive material is fixed to detect a second sample;

a trapezoidal incident structure prism on an upper portion of the micro-channel structure;

a sample injecting unit which injects a buffer solution including a first sample or a second sample into the first micro-channel and the second micro-channel, respectively;

a polarized light generating unit which irradiates incident light polarized through the trapezoidal incident structure prism onto the first micro-channel and the second micro-channel at an incident angle which satisfies a p-wave non-reflection condition; and a polarized light detecting unit which detects a polarization change of first reflected light reflected from the first sample detecting layer or the second sample detecting layer, among polarized incident light;

wherein the polarized light generating unit includes a beam splitter which divides the incident light into first incident light which is incident onto the first sample detecting layer and second incident light which is incident onto the second sample detecting layer, the first incident light and the second incident light are refracted to the first micro-channel and the second micro-channel from a lower interface of the trapezoidal incident structure prism and then divided into first reflected light reflected from the first sample detecting layer or the second sample detecting layer and second reflected light reflected by the lower interface of the trapezoidal incident structure prism and a buffer solution injected into the micro-channel, and the trapezoidal incident structure prism totally reflects the second reflected light from a planarized upper interface of the trapezoidal incident structure prism.

13. The liquid immersion micro-channel measurement device of claim 12, wherein the first sample detecting layer and the second sample detecting layer include:
a substrate;
a dielectric thin film formed above the substrate; and
an adsorption layer formed above the dielectric thin film,
a first bioadhesive material or a second bioadhesive material for detecting the first sample or the second sample is fixed to the adsorption layer.

14. The liquid immersion micro-channel measurement device of claim 13, further comprising:
a concentration calculating unit which calculates a thickness or a concentration of the first sample or the second sample which is adsorbed onto the adsorption layer based on a polarization change of the first reflected light.

15. A liquid immersion micro-channel measurement method based on trapezoidal incident structure prism incident-type silicon, the liquid immersion micro-channel measurement method comprising:
a first step of injecting a buffer solution into a micro-channel structure including at least one micro-channel having a sample detecting layer to which a first bioadhesive material is fixed to detect a first sample by a sample injecting unit;

a second step of adsorbing a first sample included in the buffer solution onto a first antibody of the sample detecting layer;

a third step of allowing a polarized light generating unit to polarize light to be incident onto the at least one micro-channel at an incident angle which satisfies a p-wave non-reflection condition, through an incident surface of a trapezoidal incident structure prism formed above the micro-channel structure;

a fourth step of allowing the polarized light detecting unit to detect a polarization change of first reflected light reflected from the sample detecting layer, among the polarized incident light; and a fifth step of detecting a concentration of a first sample adsorbed onto the sample detecting layer, based on the polarization change of the first reflected light;

wherein the trapezoidal incident structure prism totally reflects, from a planarized upper interface of the trapezoidal incident structure prism, second reflected light which is reflected from an interface of a lower interface of the trapezoidal incident structure prism and a buffer solution injected into the at least one micro-channel, among incident light which is incident onto the trapezoidal incident structure prism.

16. The liquid immersion micro-channel measurement method of claim 15, wherein in the fourth step, the polarized light detecting unit separates the first reflected light from the second reflected light.

17. The liquid immersion micro-channel measurement method of claim 15, wherein the third step further includes a step of adjusting a magnitude of the incident light which is incident through the trapezoidal incident structure prism by an optical device.

18. The liquid immersion micro-channel measurement method of claim 17, wherein the optical device further includes a reflection device including one of a lens, a lens system, and a reflector, and the third step further includes a step of forming a focal point of the incident light on the upper surface of the trapezoidal incident structure prism.

* * * * *